United States Patent [19]

Bhattacharya

[11] Patent Number: 5,489,712
[45] Date of Patent: Feb. 6, 1996

[54] PROCESS FOR PREPARING CYCLIC KETONES

[75] Inventor: Apurba Bhattacharya, Corpus Christi, Tex.

[73] Assignee: Hoechst Celanese Corporation, Somerville, N.J.

[21] Appl. No.: 334,822

[22] Filed: Nov. 4, 1994

[51] Int. Cl.⁶ .................................................. C07C 45/45
[52] U.S. Cl. ........................................ 568/312; 568/314
[58] Field of Search ..................................... 568/314, 312

[56] References Cited

U.S. PATENT DOCUMENTS

| | | | |
|---|---|---|---|
| 3,974,212 | 8/1976 | Cragoe et al. | 568/314 |
| 4,070,539 | 1/1978 | Cragoe et al. | 568/314 |
| 4,096,267 | 6/1978 | Cragoe et al. | 568/314 |
| 5,021,522 | 6/1991 | Durairaj et al. | 525/502 |
| 5,206,289 | 4/1993 | Sinsky et al. | 525/114 |

OTHER PUBLICATIONS

Ali et al, Chem. Abst., vol. 114, #143,073j (1991).

*Primary Examiner*—James H. Reamer
*Attorney, Agent, or Firm*—James J. Mullen; Donald R. Cassady

[57] ABSTRACT

The present invention provides a novel process for preparing cyclic ketones, such as indanones, which comprises the steps of (a) subjecting a substituted ketone to suitable methylenation conditions in the presence of a methylene transfer agent and an acylating agent for a sufficient period of time and under suitable conditions of temperature and pressure to form the corresponding alpha, beta unsaturated ketone, and (b) subjecting said unsaturated ketone to suitable cyclization conditions in the presence of a suitable acid or base for a sufficient period of time and under suitable conditions of temperature and pressure to form said cyclic ketones.

19 Claims, No Drawings

PROCESS FOR PREPARING CYCLIC KETONES

BACKGROUND OF THE INVENTION

1. Field of the Invention

The present invention relates to a unique, novel, and cost effective process for preparing cyclic ketones such as indanones and chromanones, and which are useful synthetic intermediates in the agrochemical as well as the pharmaceutical industries. The synthetic utility of cyclic ketones such as indanones are also enhanced by the fact that they undergo facile Robinson annulation, producing flurenones and their analogs, which exhibit important pharmacological activities.

Although the synthesis of cyclic ketones such as 2-alkyl indanones prepared by the Mannich condensation of aryl alkyl ketones with N,N,N'N'-tetramethyldiaminomethane followed by acid-catalyzed cyclization of the resulting acrylophenones is generally suggested in the prior art, its utility is limited by the prohibitively high cost of the Mannich reagent N,N,N'N'-tetramethyldiaminomethane ($[CH_3)_2N]_2CH_2$) utilized in the methylenation step. An alternate methylenation technology which involves treatment of the aryl alkyl ketones with paraformaldehyde, dimethylamine hydrochloride, and acetic acid are complicated by poor yields and unwanted by-products. Direct formation of acrylophenones via Friedel Crafts acylation on the other hand fails for electron-poor aromatics and is waste producing. Thus, there is a need to be able to produce cyclic ketones such as indanones and chromanones in an efficient, cost-effective manner and in high yields.

Description of the Prior Art

The following prior art references are disclosed in accordance with the terms of 37 CFR 1.56, 1.97, and 1.93.

U.S. Pat. No. 3,483,227 discloses pyran products and processes for preparing the same.

U.S. Pat. No. 3,974,212 discloses indanones and processes for preparing the same.

U.S. Pat. No. 4,070,539 discloses indanones and processes for preparing the same.

U.S. Pat. No. 4,096,267 discloses indanones and processes for preparing the same.

U.S. Pat. No. 4,316,043 discloses the process for preparing flurenones from indanones.

U.S. Pat. No. 4,317,922 discloses flurenones and compositions containing the same.

U.S. Pat. No. 4,587,357 discloses the process for preparing flurenones from indanones.

U.S. Pat. No. 4,605,760 discloses the preparation of enantiomers of flurenones.

*J. Org. Chem.*, Vol. 41, No. 15, 1976, pps. 2650–2651 discloses a process for preparing unsaturated ketones using the Mannich reaction.

*Journal of Medicinal Chemistry*, 1978, Vol. 21, No. 5 (pps 437–443) discloses the preparation of various indanone derivatives using the Mannich reaction.

Drug Metabolism and Disposition, 1982, Vol. 10, No. 1 (pps 20–27) discloses the pharmacological utility of various indanones.

All of the above cited prior art and any other references mentioned herein are incorporated herein by reference in their entirety.

SUMMARY OF THE INVENTION

The present invention provides a novel, unique, and efficient process for preparing cyclic ketones such as indanones and chromanones. The process comprises the steps of (a) subjecting a substituted ketone to suitable methylenation conditions in the presence of a methylene transfer agent and an acylating agent for a sufficient period of time and under suitable conditions of temperature and pressure to form the corresponding alpha, beta, unsaturated ketone, and (b) subjecting said unsaturated ketone to suitable cyclization conditions in the presence of a suitable acid or base for a sufficient period of time and under suitable conditions of temperature and pressure to form a cyclic ketone.

DETAILED DESCRIPTION OF THE INVENTION

The present invention provides a novel, unique, and efficient process for preparing cyclic ketones such as indanones and chromanones. The process comprises the steps of (a) subjecting a substituted ketone to suitable methylenation conditions in the presence of a methylene transfer agent and an acylating agent for a sufficient period of time and under suitable conditions of temperature and pressure to form the corresponding alpha, beta, unsaturated ketone, and (b) subjecting said unsaturated ketone to suitable cyclization conditions in the presence of a suitable acid or base for a sufficient period of time and under suitable conditions of temperature and pressure to form a cyclic ketone.

The starting material, i.e. the substituted ketone, has the formula:

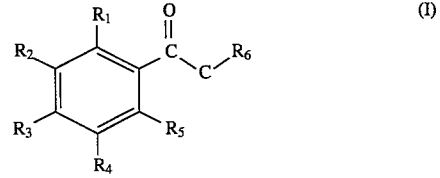

wherein (a) $R_1$, $R_2$, $R_3$, and $R_4$ are either alike or unlike and are each selected from the group consisting of H, halogen, alkoxy, alkyl ($C_{1-8}$), phenyl, naphthyl, and substituted phenyl or naphthyl; (b) $R_5$ is selected from the group consisting of H, OH, SH, and $NHR_7$, wherein $R_7$ is alkyl ($C_{1-8}$); and (c) $R_6$ is selected from the group consisting of alkyl ($C_{1-8}$), phenyl, naphthyl, substituted phenyl or naphthyl, and $COOR_8$, wherein $R_8$ is H or alkyl ($C_{1-8}$). Halogen includes Cl, F, Br, I, and the like. Alkoxy includes $-OCH_3$, $-OC_2H_5$, $-OC_3H_7$, $-OC_4H_9$, and the like.

Utilizing the substituted ketone (Formula I), it is believed that the process proceeds as shown in Scheme 1 below:

Scheme 1

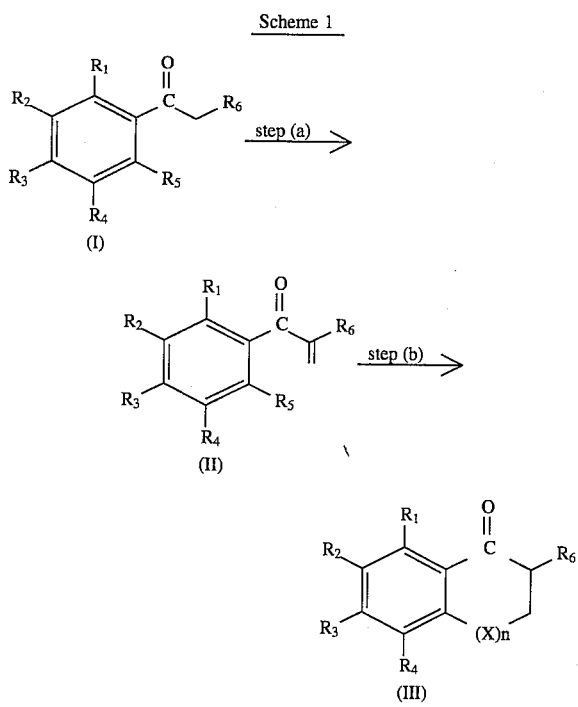

In Scheme 1, step (a) corresponds to that step (a) mentioned herein and where the substituted ketone is subjected to suitable methylenation conditions in the presence of a methylene transfer agent and an acylating agent for a sufficient period of time and under suitable conditions of temperature and pressure to form the corresponding alpha, beta, unsaturated ketone such as acrylophenones.

The methylene transfer agent (MTA) used is critical. To produce the cyclic ketones, it is critical that hexamethylenetetramine (HMTA) be used. In this manner, the low cost process can be achieved. It has been found that numerous amine products do not work in the process outlined herein. For example, dimethylamine, diethylamine, and other dialkylamines, when used as MTA, do not perform the desired intended task.

The amount of MTA employed is any amount which would produce the desired end result. Generally, this amount would be in the range of from about 0.2 to about 4.0 moles per mole of starting material; i.e. the substituted ketone.

The acylating agent employed in step (a) of the process is any acid anhydride or any acid halide. The acid anhydride has the formula:

wherein $R_{10}$ and $R_{11}$ are alkyl $C_{1-8}$ or aromatic anhydrides and include, without limitation, such anhydrides as acetic anhydride, propionic anhydride, butyric anhydride, valeric anhydride, hexanoic anhydride, and benzoic anhydride. It is to be understood that the acylating agent is a term which means that the material is an electrophile and, as such, includes species such as (a) acylating agents such as acid anhydrides and acid halides; and (b) Lewis acids.

The acid halides which can be used have the formula:

wherein $R_{12}$ is alkyl $C_{1-8}$ and X is halogen such as Cl, F, and Br and include, without limitation, acetyl chloride.

The amount of acetylating agent employed is any amount which would produce the desired end result. Generally, this amount would be in the range of from about 0.1 to about 8.0 moles per mole of starting material, i.e. the substituted ketone.

One of the critical features of the present invention process is the fact that the acylating agent employed must not be in the acid form in order to achieve the desired end result. For example, where one uses acetic anhydride, the reaction proceeds smoothly and at high yields. Whereas, where one uses acetic acid, the reaction does not work.

The temperature at which step (a) is conducted ranges from about 50° C. to about 300° C., preferably from about 60° C. to about 200° C. The pressure in this step (a) is not critical and can be subatmospheric; atmospheric, or super atmospheric.

The reaction times in step (a) will generally range from about ¼ hour to about 12 hours or longer and sometimes under an inert atmosphere such as nitrogen.

Using the procedure of step (a) outlined herein, the substituted ketone undergoes suitable methylenation conditions to form the corresponding alpha, beta unsaturated ketone, Formula II.

In Scheme 1, step (b) corresponds to that step (b) (a second step) mentioned herein and this is where the alpha, beta unsaturated ketone (the intermediate product) Formula II is subjected to suitable cyclization conditions in the presence of a suitable acid or base for a sufficient period of time and under suitable conditions of temperature and pressure to form the desired cyclic ketones.

The suitable acid is any material which will function for the cyclization conditions and includes, without limitation, mineral acids such as HCl and $H_2SO_4$. The suitable base is any material which will function for the cyclization conditions to produce the desired end product, e.g. chromanones, and chromanone derivatives. A suitable base includes an inorganic base such as a metal hydroxide, preferably an alkali metal hydroxide, an alkali metal carbonate, e.g. $K_2CO_3$; an alkali metal alkoxide (an ionic organic base) such as $NaOCH_3$, $KOC(CH_3)_3$, etc.; an alkali metal organic acid salt (an ionic organic base) such as potassium acetate, etc.; and an amine (a non-ionic organic base) such as pyridine or a tri-lower-alkylamine, e.g. tripropylamine, trimethylamine, and triethylamine, etc.

The amount of acid or base employed in step (b) is from about 0.1 moles to about 6 moles per mole of starting material, i.e. the substituted ketone. The preferred amount is from about 1 mole to about 4 moles per mole of starting material.

The temperature at which step (b) is conducted ranges from about 20° C. to about 200° C., preferably from about 40° C. to about 150° C. The pressure in this step (b) is not critical and can be subatmospheric, atmospheric, or super atmospheric.

The reaction times in step (b) will generally range from about ¼ hour to about 12 hours or longer and sometimes under an inert atmosphere such as nitrogen.

Using the procedure of step (b) outlined herein, the alpha, beta unsaturated ketone undergoes suitable cyclization conditions to form the corresponding cyclic ketone, Formula III.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLES 1–8

The following procedure was used to prepare certain 2-alkyl indanones except that the starting ketone was different in each example.

A mixture of propiophenone (30 g, 223.6 mmol) hexamethylenetetramine (HMTA) (43.8 g, 313 mmol) and acetic anhydride (41 g, 402 mmol) was heated at 80° C. for 4 hours under a nitrogen atmosphere. The reaction mixture was cooled to 30° C. and quenched into a stirred mixture of methylene chloride (200 ml) and sodium hydroxide (200 of 2N solution). The organic layer was separated and washed with aqueous HCl (100 ml of 1N solution). The methylene chloride solution containing the product, 2-methyl-1-phenyl-prop-2-en-1-one was azeotropically dried by distilling $CH_2Cl_2$ to approximately 50 ml volume and was directly used in the next step without any further operation. The $CH_2Cl_2$ solution was added to concentrated $H_2SO_4$(130 ml) at such a rate that the reaction temperature was maintained between 50°–60° C. The $CH_2Cl_2$ was removed by distillation and nitrogen sweep as soon as it was added. The reaction mixture was stirred at 50°–60° C. for one hour, cooled to 20° C. and quenched into a stirred mixture of methylene chloride (200 ml) and water (200 g). After separating the aqueous layer, the organic layer was concentrated in the rotary evaporator to produce 121 g (82%) of 2-methyl-inden-1-one (Example 1, Table 1).

The results of using the above procedure are disclosed in Table 1.

TABLE 1

Preparation of 2-Alkylindanones[a]

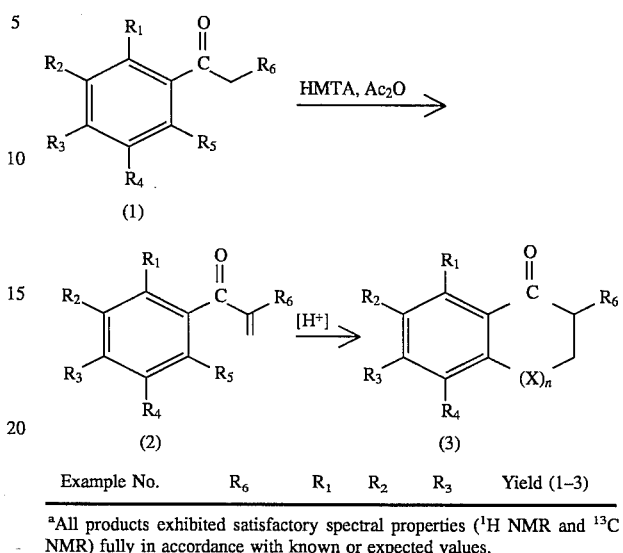

| Example No. | $R_6$ | $R_1$ | $R_2$ | $R_3$ | Yield (1–3) |
|---|---|---|---|---|---|
| 1 | Me | H | H | H | 82% |
| 2 | Et | H | H | H | 80% |
| 3 | n-Bu | H | H | H | 86% |
| 4 | Me | H | Br | H | 82%[b] |
| 5 | n-Octyl | H | H | H | 87% |
| 6 | n-Propyl | Cl | Cl | OMe | 84% |
| 7 | Ph | Cl | Cl | OMe | 76% |
| 8 | Me | H | H | OMe | 78% |

TABLE 1-continued

Preparation of 2-Alkylindanones[a]

[a]All products exhibited satisfactory spectral properties ($^1$H NMR and $^{13}$C NMR) fully in accordance with known or expected values.
[b]1:1 Mixture of the two regioisomeric cyclized products (4-bromo and 6-bromo) was obtained. $R_4$ and $R_5$ were both hydrogen.

EXAMPLE 9 (Comparative)

Example 1 is repeated except that the equivalent millimoles of acetic acid are used instead of acetic anhydride. NMR analyses shows that no cyclic ketone is produced.

EXAMPLE 10 (Comparative)

Example 1 is repeated except that the equivalent millimoles of dimethylamine are used instead of hexamethylenetetramine (HMTA). NMR analyses shows that no cyclic ketone is produced.

EXAMPLE 11 (Comparative)

Example 1 is repeated except that the equivalent millimoles of diethylamine are used instead of HMTA. NMR analyses shows that no cyclic ketone is produced.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

I claim:

1. A process for preparing cyclic ketones which comprises the steps of (a) subjecting a substituted ketone to suitable methylenation conditions in the presence of hexamethylenetetramine and an acylating agent for a sufficient period of time and under suitable conditions of temperature and pressure to form the corresponding alpha, beta unsaturated ketone, and (b) subjecting said unsaturated ketone to suitable cyclization conditions in the presence of a suitable acid or base for a sufficient period of time and under suitable conditions of temperature and pressure to form said cyclic ketones.

2. The process as set forth in claim 1 wherein the substituted ketone has the formula:

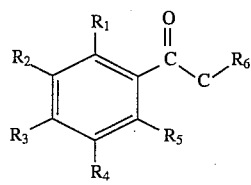

wherein (a) $R_1$, $R_2$, $R_3$, and $R_4$ are either alike or unlike and are each selected from the group consisting of H, halogen, alkoxy, alkyl ($C_{1-8}$), phenyl, naphthyl, substituted phenyl and substituted naphthyl; (b) $R_5$ is selected from the group consisting of H, OH, SH, and $NHR_7$, wherein $R_7$ is alkyl ($C_{1-8}$); and (c) $R_6$ is selected from the group consisting of alkyl ($C_{1-8}$), phenyl, naphthyl, substituted phenyl and naphthyl, and $COOR_8$, wherein $R_8$ is H or alkyl ($C_{1-8}$).

3. A process as set forth in claim 1 wherein the cyclic ketones have the formula:

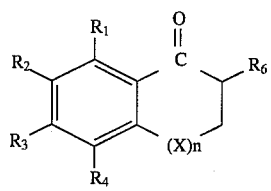

wherein (a) $R_1$, $R_2$, $R_3$, and $R_4$ are either alike or unlike and are each selected from the group consisting of H, halogen, alkoxy, alkyl ($C_{1-8}$), phenyl, naphthyl, substituted phenyl, and substituted naphthyl; (b) $R_5$ is selected from the group consisting of alkyl ($C_{1-8}$), phenyl, naphthyl, substituted phenyl, and substituted naphthyl, and $COOR_8$, wherein $R_8$ is H or alkyl, ($C_{1-8}$); (c) X is selected from the group consisting of oxygen, nitrogen, and sulfur; and (d) n is 0 or 1.

4. The process as set forth in claim 3 wherein n is 0.

5. The process as set forth in claim 3 wherein n is 1 and X is oxygen.

6. The process as set forth in claim 3 wherein n is 1 and X is nitrogen.

7. The process as set forth in claim 3 wherein n is 1 and X is sulfur.

8. The process as set forth in claim 1 wherein in step (a) the temperature is from about 50° C. to about 300° C. and the pressure is atmospheric; and in step (b) the temperature is from about 20° C. to about 200° C. and the pressure is atmospheric.

9. The process as set forth in claim 8 wherein in step (a) the temperature is from about 80° C. to about 200° C.; and in step (b) the temperature is from about 40° C. to about 150° C.

10. A process for preparing aryl alkyl indanones which comprises the steps of (a) subjecting an aryl alkyl ketone to suitable methylenation conditions in the presence of hexamethylenetetramine and an acylating agent for a sufficient period of time and under suitable conditions of temperature and pressure to form an acrylophenone; and (b) subjecting said acrylophenone to suitable cyclization conditions in the presence of a suitable acid or base for a sufficient period of time and under suitable conditions of temperature and pressure to form said aryl alkyl indanones.

11. The process as set forth in claim 10 wherein the aryl alkyl ketone has the formula:

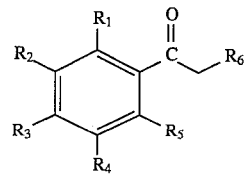

wherein (a) $R_1$, $R_2$, $R_3$, and $R_4$ are either alike or unlike and are each selected from the group consisting of H, halogen, alkoxy, alkyl ($C_{1-8}$), phenyl, naphthyl, substituted phenyl, and substituted naphthyl; (b) $R_5$ is hydrogen; and (c) $R_6$ is selected from the group consisting of alkyl ($C_{1-8}$), phenyl, naphthyl, substituted phenyl, substituted naphthyl, and $COOR_7$, wherein $R_7$ is H or alkyl ($C_{1-8}$).

12. The process as set forth in claim 10 wherein the aryl alkyl indanones have the formula:

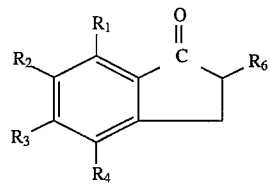

wherein (a) $R_1$, $R_2$, $R_3$, and $R_4$ are either alike or unlike and are each selected from the group consisting of H, halogen, alkoxy, alkyl ($C_{1-8}$), phenyl, naphthyl, substituted phenyl, and substituted naphthyl; and (b) $R_6$ is selected from the group consisting of alkyl ($C_{1-8}$), phenyl, naphthyl, substituted phenyl, substituted naphthyl, and $COOR_7$, wherein $R_7$ is H or alkyl ($C_{1-8}$).

13. The process as set forth in claim 10 wherein in step (a) the temperature is from about 50° C. to about 300° C. and the pressure is atmospheric; and in step (b) the temperature is from about 20° C. to about 200° C. and the pressure is atmospheric.

14. The process as set forth in claim 13 wherein in step (a) the temperature is from about 80° C. to about 200° C.; and in step (b) the temperature is from about 40° C. to about 150° C.

15. The process as set forth in claim 10 wherein the acylating agent is selected from the group consisting of acid anhydrides and acid halides.

16. The process as set forth in claim 15 wherein the acylating agent is acetic anhydride.

17. The process as set forth in claim 15 wherein the cyclization conditions include a suitable acid.

18. The process as set forth in claim 15 wherein the cyclization conditions include a suitable base.

19. The process as set forth in claim 15 wherein the indanones prepared are 2-alkyl indanones.

* * * * *